(12) United States Patent
Holte

(10) Patent No.: US 6,322,514 B1
(45) Date of Patent: Nov. 27, 2001

(54) METHOD FOR DETERMINING CARDIAC CHARACTERISTICS OF SUBJECT

(75) Inventor: Bo Holte, Charlottenlund (DK)

(73) Assignee: Instrumentarium Corporation

( * ) Notice: Subject to any disclaimer, the term of this patent is extended or adjusted under 35 U.S.C. 154(b) by 0 days.

(21) Appl. No.: 09/524,646

(22) Filed: Mar. 13, 2000

(51) Int. Cl.⁷ ...................................................... A61B 5/02
(52) U.S. Cl. ........................... 600/481; 600/538; 600/561
(58) Field of Search ...................................... 600/481, 483, 600/484, 508, 529, 538; 128/204.18, 204.21, 204.23

(56) References Cited

U.S. PATENT DOCUMENTS

| | | |
|---|---|---|
| 4,137,910 | 2/1979 | Murphy . |
| 4,437,469 | 3/1984 | Djordjevich et al. . |
| 4,450,527 | 5/1984 | Sramek . |
| 4,643,192 | 2/1987 | Fiddian-Green . |
| 4,676,253 | 6/1987 | Newman et al. . |
| 4,870,578 | 9/1989 | Vysin et al. . |
| 4,893,630 * | 1/1990 | Bray, Jr. ............................. 600/484 |
| 5,025,795 | 6/1991 | Kunig . |
| 5,043,576 | 8/1991 | Broadhurst et al. . |
| 5,052,395 | 10/1991 | Burton et al. . |
| 5,085,220 | 2/1992 | Nudell et al. . |
| 5,101,828 | 4/1992 | Welkowitz et al. . |
| 5,174,290 | 12/1992 | Fiddian-Green . |
| 5,183,051 | 2/1993 | Kraidin et al. . |
| 5,186,172 | 2/1993 | Fiddian-Green . |
| 5,241,966 | 9/1993 | Finkelstein et al. . |
| 5,265,615 | 11/1993 | Frank et al. . |
| 5,390,679 | 2/1995 | Martin . |
| 5,458,128 | 10/1995 | Polanyi et al. . |
| 5,469,859 | 11/1995 | Tsoglin et al. . |
| 5,494,031 | 2/1996 | Hoeft . |
| 5,535,753 | 7/1996 | Petrucelli et al. . |
| 5,575,289 | 11/1996 | Skidmore . |
| 5,584,298 | 12/1996 | Kabal . |
| 5,647,369 | 7/1997 | Petrucelli et al. . |
| 5,685,316 | 11/1997 | Schookin et al. . |
| 5,782,774 | 7/1998 | Shmulewitz . |
| 5,836,300 | 11/1998 | Mault . |
| 5,876,347 | 3/1999 | Chesney et al. . |

FOREIGN PATENT DOCUMENTS

| | | |
|---|---|---|
| 10-94528 | 4/1998 | (JP) . |
| 97/47236 | 12/1997 | (WO) . |
| 98/12963 | 4/1998 | (WO) . |
| 98/26710 | 6/1998 | (WO) . |
| 98/51212 | 11/1998 | (WO) . |
| 98/56291 | 12/1998 | (WO) . |
| 99/23941 | 5/1999 | (WO) . |

* cited by examiner

Primary Examiner—Robert L. Nasser
Assistant Examiner—Navin Natnithithadha
(74) Attorney, Agent, or Firm—Andrus, Sceales, Starke & Sawall, LLP

(57) ABSTRACT

A non-invasive method for determining the stroke volume of the heart, i.e. the volume of blood discharged per heart beat. A pressure transducer, is placed in a hollow organ, such as the lungs, stomach or bladder of a subject. During ventilation of, or breathing by, the subject, the incremental change in pressure in the hollow organ resulting from an incremental change in breathing gas volume in the subject's lungs is obtained and a ratio between the two is established. The pressure change in the hollow organ caused by volumetric changes resulting from the contraction of the subject's heart when discharging blood is also measured. The stroke volume of the subject's heart is determined by applying the volume/pressure ratio to the pressure change resulting from the contraction of the heart.

31 Claims, 8 Drawing Sheets

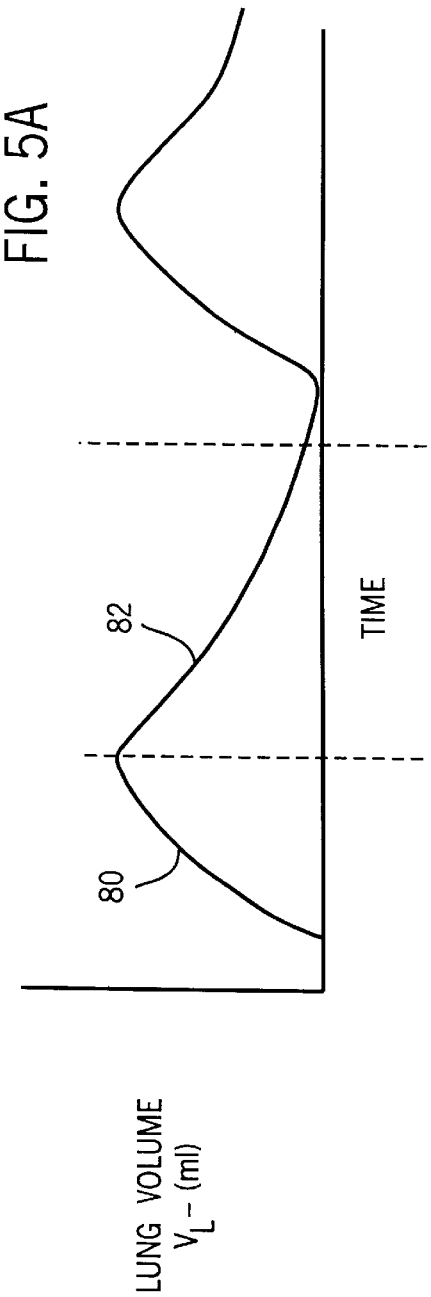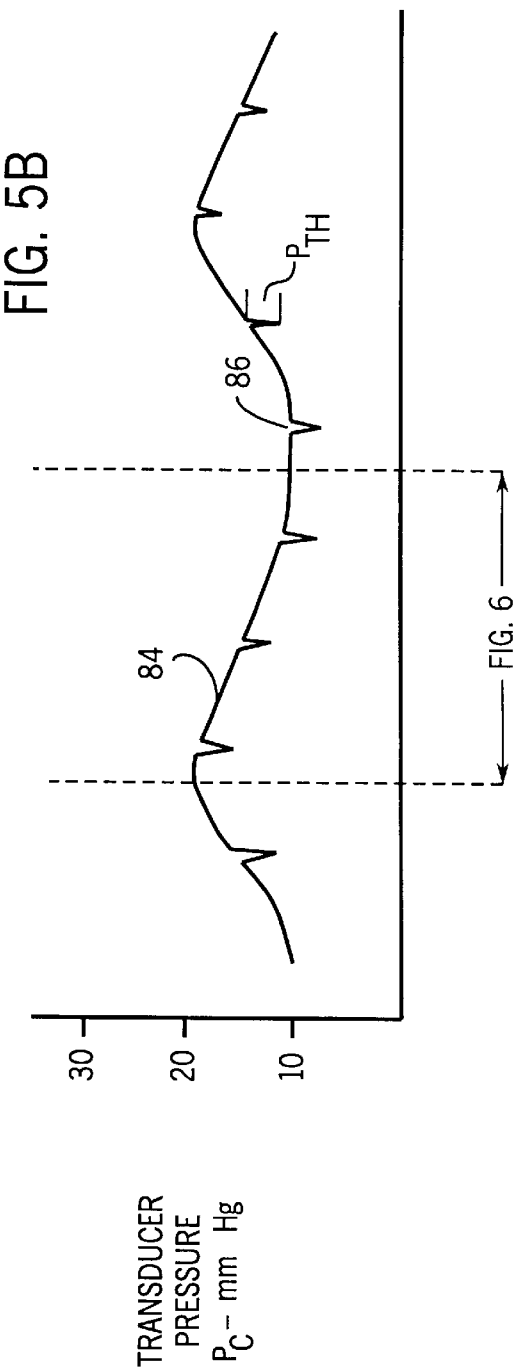

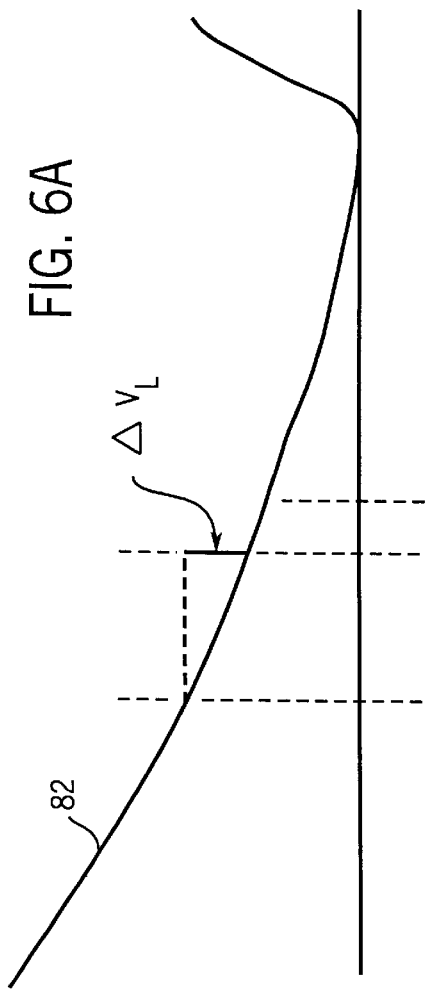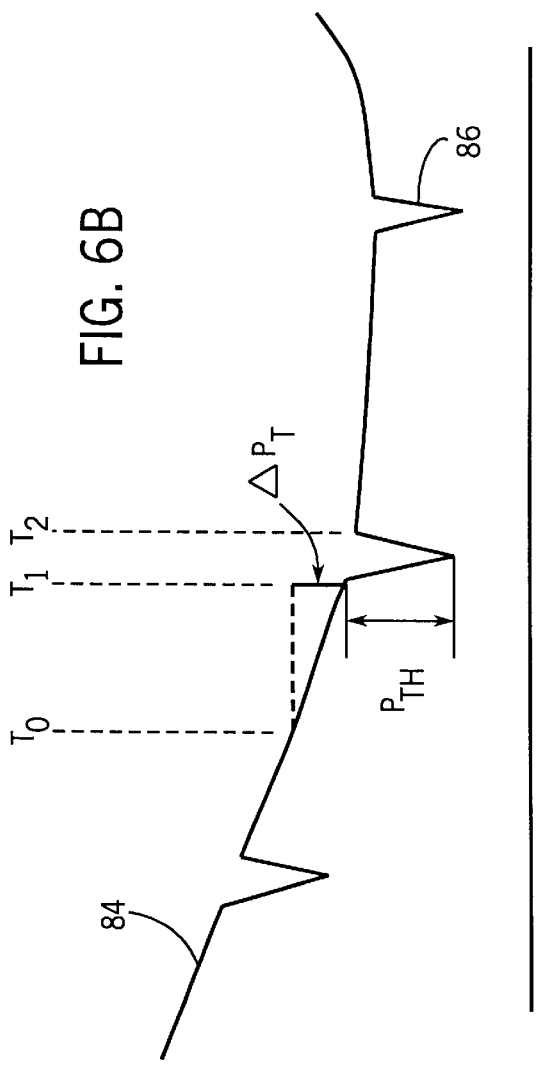

METHOD FOR DETERMINING CARDIAC CHARACTERISTICS OF SUBJECT

BACKGROUND OF THE INVENTION

The present invention relates to a method for determining physiological characteristics produced by the functioning of the heart, such as stroke volume and cardiac output. The method of the present invention may provide absolute, as contrasted to relative, values of these characteristics.

In many instances, such as prior, during, or following major surgery, it is important to determine certain physical characteristics of a patient's heart. For example, it may be necessary or desirable to determine the volume of blood being discharged from the patient's heart. The volume may be expressed as the stroke volume (SV), which is the volume of blood discharged during each contraction or beat of the heart, or the cardiac output (CO), which is the volume of blood discharged over a given period of time, such as a minute. Or, it may be necessary or desirable to know atrial and/or ventricular ejection times in order to assess the contractility of the heart muscle.

The most direct way to measure these quantities is to use a pulmonary artery catheter. Such a catheter is surgically positioned inside the heart in a pulmonary artery catheterization procedure. However, such positioning is a highly invasive, labor intensive procedure which requires a high level of surgical skill and which places a patient at considerable risk. For these reasons, attempts have been made to develop less invasive, or non-invasive, methods for determining the amount of blood discharged from a patient's heart.

Approaches taken to this end include the following. Some methods use changes in the electrical impedance of the thorax, as measured by electrodes placed on the patient's skin to determine cardiac functioning. See U.S. Pat. Nos. 5,782,774; 5,685,316; 5,469,859; 4,870,578; 4,450,527; and 4,437,469. Other methods employ ultrasonic probes. For example, such probes may be placed in the suprastenal notch or in the esophagus to measure blood flow in the aorta. See U.S. Pat. Nos. 5,575,289; 5,085,220; 5,052,395; and WO 98/51212. Another approach is to apply various algorithms to the blood pressure waveform to determine cardiac output. See U.S. Pat. Nos. 5,876,347; 5,647,369; 5,584,298; 5,535,753; 5,390,679; 5,265,615; 5,241,966; 5,183,051; 5,101,828; 5,025,795; 4,676,253; 4,137,910 and WO 97/47236 and Japanese Patent Publication 10-094528. Dye dilution techniques have also been employed in which a dye is injected into the blood stream and a sensor detects the dye concentration in the blood after the dye has passed through the heart. See U.S. Pat. Nos. 5,494,031 and 5,458,128. In a technique, commonly called the Fick method, $CO_2$ is measured in the air expired by the patient and used to make a determination of the volume of blood discharged by the patient. See U.S. Pat. Nos. 5,836,300 and 5,043,576 and WO 98/26710 and WO 98/12963.

However, a problem with one or more of the foregoing methods is that they may produce inaccurate results due, for example, to the use of less than correct assumptions in deriving an algorithm for determining volumes from the shape of a blood pressure waveform. Further, the methods determine only a relative blood volume value. In order to produce an absolute blood output value, a calibration value obtained by a pulmonary artery catheter is required.

BRIEF SUMMARY OF THE INVENTION

It is, therefore, the object of the present invention to provide an improved method for determining functional characteristics of the heart, such as stroke volume and cardiac output, ejection times and the like.

The method of the present invention can be characterized as non-invasive when contrasted to invasive procedures that require surgical intervention into the heart or a blood vessel of the subject. The method of the present invention may provide absolute, as contrasted to relative, values for the blood volume characteristics.

A further feature of the present invention is that tonometric measurements of partial gas pressure in a hollow organ of the subject may be combined with the determination of cardiac characteristics.

The method of the present invention employs to unique advantage the phenomenon that volumetric changes in the thoracic cavity, such as those accompanying respiration or the beating of the heart, are reflected as pressure changes in other hollow organs of the body, such as the esophagus, stomach, or bladder. In the case of the lungs, volumetric changes occurring during the beating of the heart are reflected as pressure changes in the lungs.

To carry out the method of the present invention, a pressure transducer is placed in the hollow organ. During a sampling interval, the volume of breathing gases supplied to/removed from the lungs of the subject is measured to obtain the incremental quantity of breathing gas $\Delta V_L$ supplied or removed during the interval. The supply or removal of breathing gases alters the volume or size of the lungs in the thoracic cavity. During the same sampling interval, the pressure change in the hollow organ resulting from the change in lung volume $\Delta VL$ is also measured, as pressure $\Delta P_T$, using the pressure transducer. A relationship, or ratio, between volumetric changes in the thoracic cavity and pressure changes in the hollow organ is established as $\Delta V_L/\Delta P_T$.

The contraction of the heart when discharging blood also comprises a volumetric change in the thorax. In a second sampling interval, the reduction in hollow organ pressure resulting from the contraction of the heart when discharging blood is obtained as $P_{TH}$. Knowing this pressure reduction $P_{TH}$ and the relationship between volumetric changes in the thoracic cavity and pressure changes in the hollow organ, as expressed by the relationship $\Delta V_L/\Delta P_T$, the volumetric reduction in the size of the heart during contraction, and hence its stroke volume, can be quantified as an absolute value by applying the latter to the former. The cardiac output (CO) of the heart can be ascertained by determining and summing the stroke volumes of the heart beats occurring in a given period of time, such as one minute. Ejection times can be measured by analyzing the temporal properties of the reduction in hollow organ pressure resulting from the contraction of the heart.

The pressure measurements in the hollow organs may be obtained with a catheter, filled with gas or liquid, and containing the pressure transducer. Such a catheter may also be used to carry out tonometric measurements in the hollow organ.

Various other features, objects, and advantages of the invention will be made apparent from the following detailed description and the drawing.

BRIEF DESCRIPTION OF THE SEVERAL VIEWS OF THE DRAWING

The invention will be better understood by reference to the following detailed description and the accompanying drawing in which:

FIGS. 5A and 5B are similar to FIGS. 4A and 4B and FIG. 5B shows the effect of the beating of the heart on the pressure sensed by the pressure transducer;

FIGS. 6A and 6B are the enlarged portion of FIGS. 5A and 5B identified in FIG. 5;

DETAILED DESCRIPTION OF THE PREFERRED EMBODIMENTS

The trunk, or torso, of the body includes a thoracic cavity and an abdominal cavity separated by the diaphragm. The thoracic cavity contains the heart and lungs. The abdominal cavity includes the organs of the digestive system, such as the stomach and intestines; the excretory system, such as the bladder and kidneys; and other organs.

Figure 1:
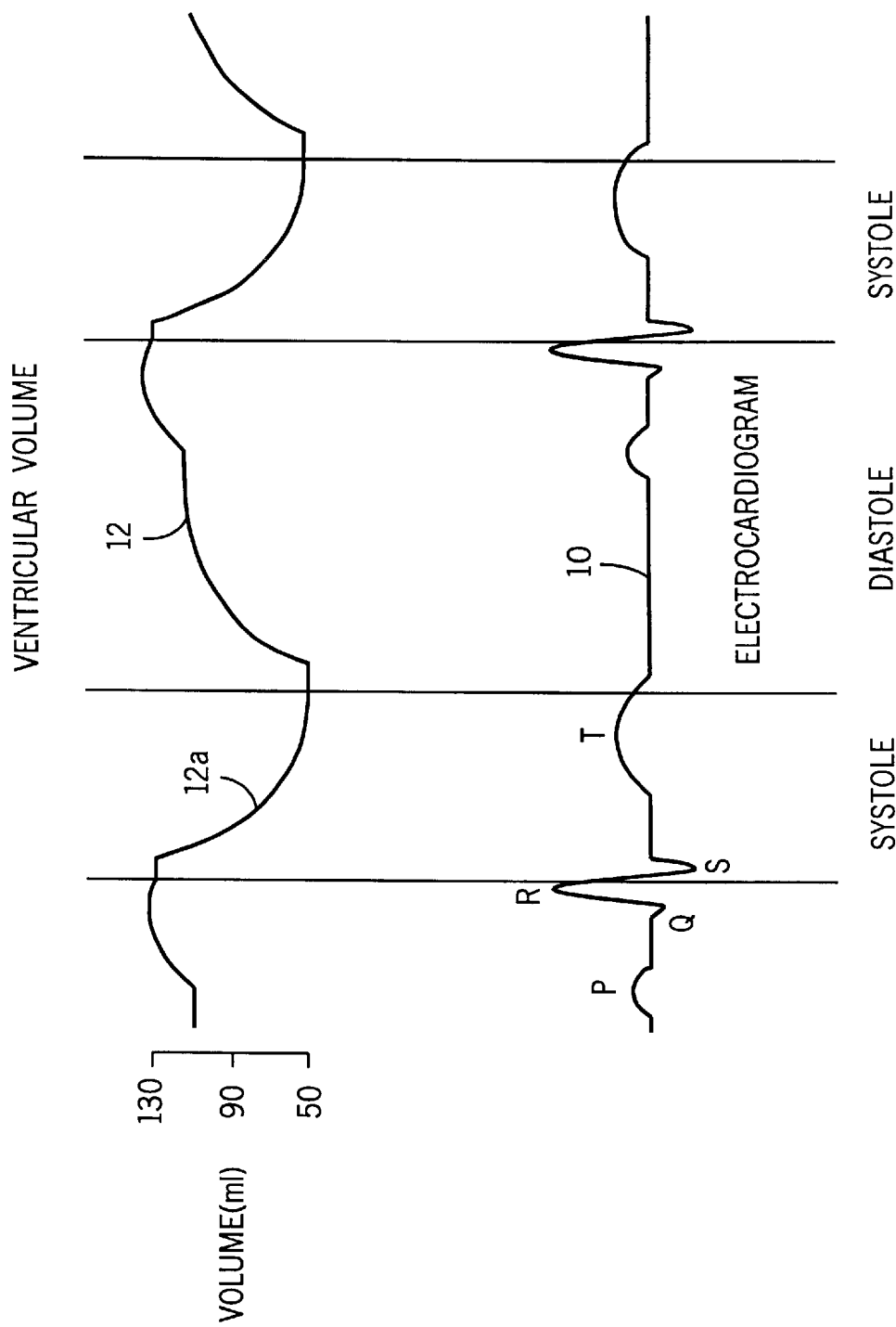
FIG. 1 is a graph showing an electrocardiogram and changes in ventricular volume associated with the physiological functioning of the heart.

The heart serves as a pump to circulate blood through the arteries and veins of the body. The heart has atria that receive blood and ventricles that discharge blood. The heart alternately contracts, during systole, to expel blood from the ventricles into the arteries and relaxes or expands, during diastole, to receive blood from the veins into the atria for discharge during the next contraction. The periodic operation of the heart is shown in FIG. 1. Graph 10 is a conventional electrocardiogram showing the electrical activity associated with the physiological functioning of the heart including the QRS complex attendant the intiation of systolic action and the T-wave near the end of the systole. Graph 12 shows changes in the ventricular volume of the heart in milliliters (ml). The reduction in the size of the heart during the contractive, systolic phase in which blood is discharged from the heart is shown by 12a.

A typical heart rate is 60–80 operations, or beats, per minute. This is about one beat per second or every 1000 milliseconds (ms). The quiescent, diastolic interval is about 400 ms. The period of ventricular, systolic contraction occupies about 400 ms. About 80 ml of blood is discharged from the ventricles during the systole. By an analogy to the operation of other mechanical pumps, the amount of blood discharged from the heart during each contraction, or beat is termed the stroke volume (SV).

The lungs are two cone-shaped, spongy organs that contain alveoli that circulate air or other breathing gases for gas exchange with the blood. During normal inspiration, or inhalation, the diaphragm moves downward, i.e. away from the neck, and the ribcage expands allowing the lungs to inflate and expand. On expiration or exhalation, the diaphragm moves up and the ribcage contracts forcing air out of the lungs.

A typical unassisted breathing rate is 12–22 breaths per minute, or about one breath every 3–5 seconds. A typical amount of air breathed in and out, termed tidal volume ($V_T$), is 400–700 milliliters (ml). With mechanically assisted breathing, the breathing rate and volume are determined by a ventilator but are generally those resembling the natural breathing action.

In the method of the present invention, a pressure transducer probe is placed in fluid communication with a hollow organ of a subject's body for sensing pressures in the hollow organ. If the hollow organ is the lungs, the probe may be at a desired location along the pathway for breathing gases to and from the lungs of the subject. For example, if the subject is intubated with an endotracheal tube, the probe may be located proximate the distal end of the endotracheal tube. The pressure transducer may comprise a piezoelectric or other suitable pressure sensing element.

It is known that volumetric changes occurring in the lungs during breathing can be seen in other organs of the body. As the lungs expand in size during inspiration, other organs in the body are compressed by this expansion, increasing the internal pressure of the other organs. This phenomenon is particularly present in hollow organs both above the diaphragm, such as the esophagus, and below the diaphragm, such as the stomach or urinary bladder. This phenomenon allows the use of such other hollow organs in the method of the present invention.

Figure 2:
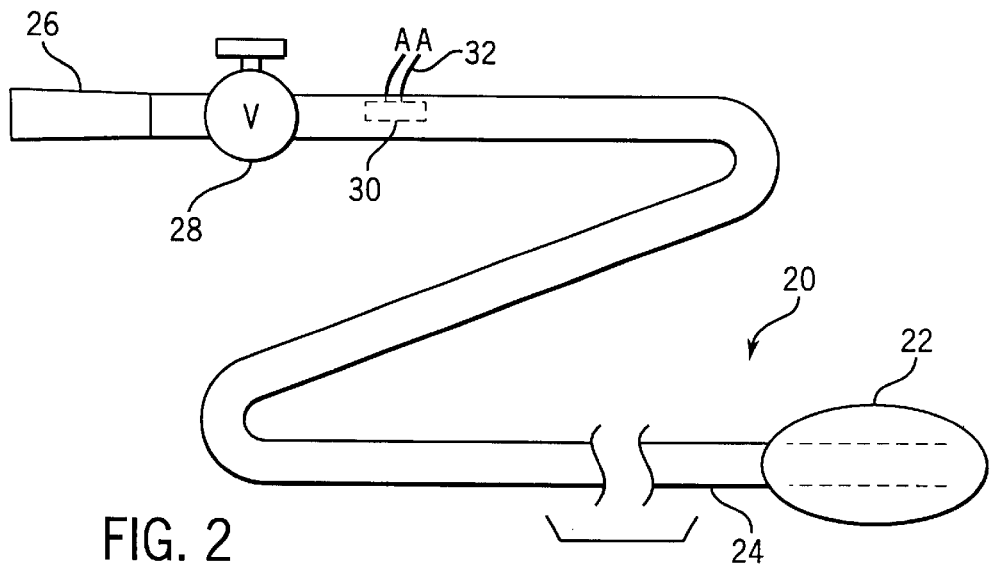
FIG. 2 shows one embodiment of a pressure transducer suitable for carrying out the method of the present invention.

FIG. 2 shows one embodiment of a pressure transducer device suitable for carrying out the method of the present invention using the stomach as the hollow organ in which pressure is sensed. The device is in the form of a catheter 20 having an inflatable balloon 22 at one end of tube 24. Catheter 20 is inserted in the stomach in the deflated condition with the second end of the tube remaining outside of the body. The catheter can be inserted through the nose and esophagus of the subject. Balloon 22 and the lumen of tube 24 are then filled with a fluid, as from a syringe inserted in luer lock 26, to inflate the balloon. Valve 28 is closed to retain the fluid in the catheter. Balloon 22 and tube 24 may be filled with a gas, such as air, or a liquid, such as water. The fluid in balloon 22 and tube 24 transmits pressures existing in the hollow organ to pressure transducer 30 at the second end of tube 24.

The output of the pressure transducer in the probe or catheter is provided to a computational circuit, which may be a microprocessor. In the case of catheter 20 shown in FIG. 2, the output of pressure transducer 30 is provided in conductor 32 to computational circuit 33, shown in FIG. 3, as indicated by the connection A—A.

While the placement of the catheter as described above is within the body of the subject, it is not "invasive" in the conventional sense of the term as connoting use of surgical instruments and intervention.

The method of the present invention may be carried out either with a spontaneously breathing subject or with the subject mechanically ventilated. In mechanical ventilation, a ventilator supplies a volume of breathing gas to the subject during the inspiration phase of each breath to inflate the lungs of the patient. The lungs of the patient are deflated, during expiration, either by the natural action of the subject's chest wall and diaphragm or under the control of the ventilator. The deflation of the lungs removes a breathing gas volume from the lungs. The invention is described below in connection with mechanical ventilation.

Figure 3:
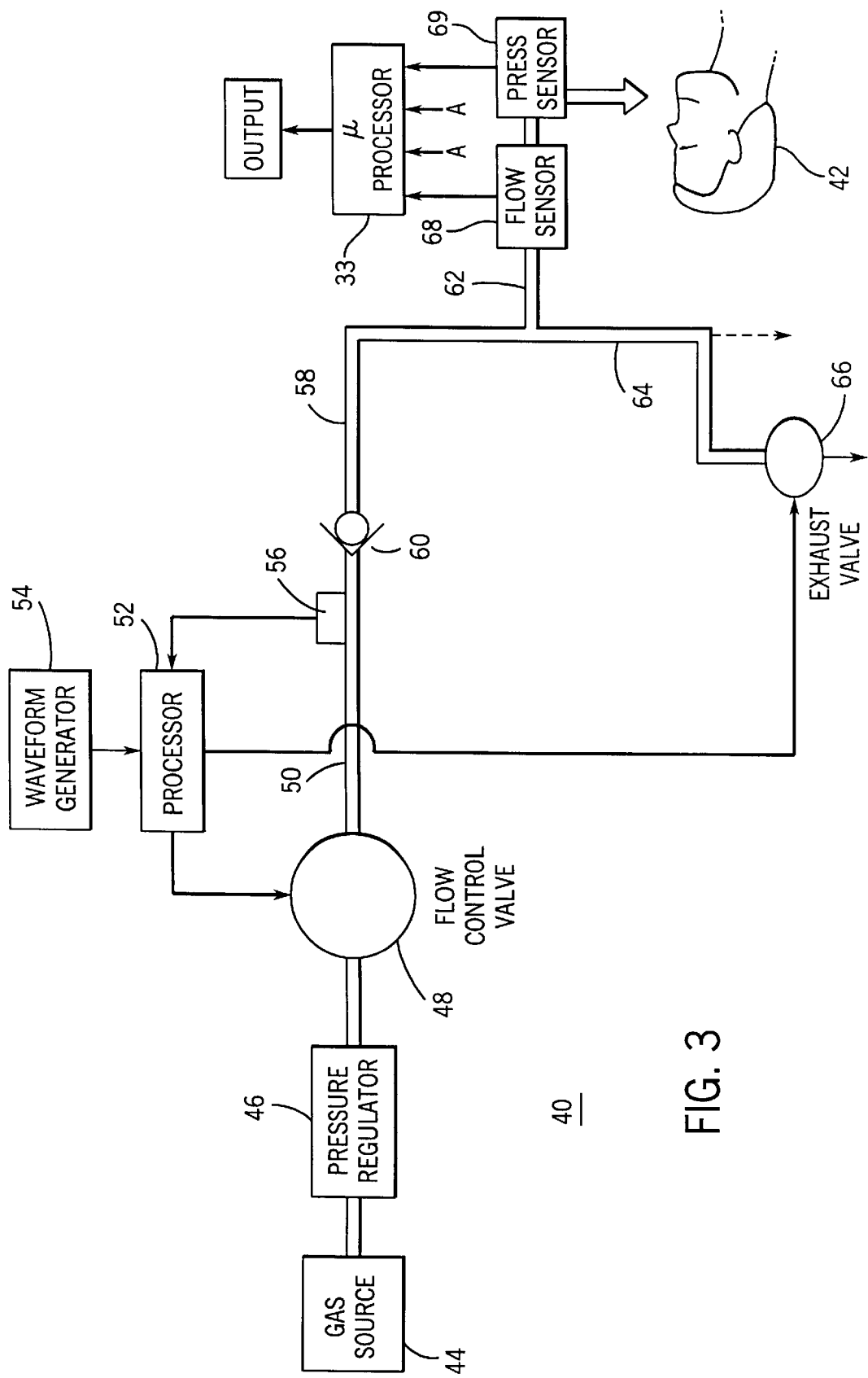
FIG. 3 shows one embodiment of ventilator apparatus suitable for use in the method of the present invention.

FIG. 3 shows, in simplified form, a ventilator 40 suitable for providing breathing gases or "ventilating" a subject 42. The ventilator shown in FIG. 3 is of the open type in which the breathing gases exhaled by the patient 42 are exhausted to the atmosphere. However, the present invention may be practiced with other types of ventilators, such as the closed circuit ventilator shown in FIG. 9 in which exhaled breathing gases are re-breathed. Ventilator 40 is connected to a breathing gas source 44 which may be a pressurized gas cylinder or cylinders, or a hospital manifold. The gas from source 44 is supplied through pressure regulator 46 to flow control valve 48 in conduit 50. Flow control valve 48 may comprise a proportional control valve. The operation of valve 48 is controlled by controller 52 which may be a microprocessor. Controller 52 is, in turn, controlled by waveform generator 54 which provides a desired breathing gas pressure waveform to controller 52 for use in operating valve 48 to provide breathing gases from source 44 to subject 42. A pressure feedback signal from pressure sensor 56 is also provided to controller 52.

Conduit 50 communicates with conduit 58 and provides inspiration breathing gas flow to subject 42 through check valve 60 and conduit 62. Conduit 62 is connected to an endotracheal tube or face mask for patient 42 that supplies and receives breathing gases to and from subject 42.

The expiratory breathing gases exhaled from patient received in conduit 62 may be discharged directly to the ambient atmosphere by the natural breathing action of subject 42. Or the breathing gases may pass through conduit 64 and valve 66. Valve 66 is controlled by controller 52 to control the exhalation of breathing gases in a desired manner, to provide positive end expiration pressure (PEEP), or for other purposes.

Flow sensor 68 is mounted in conduit 62 to measure the volume of gas inspired and expired by subject 42. Flow sensor 68 may sense the flow volume by means of the pressure drop across a laminar flow, or other, restrictor in conduit 62. Flow sensor 68 is also connected to computational circuit 33.

Figure 4A:
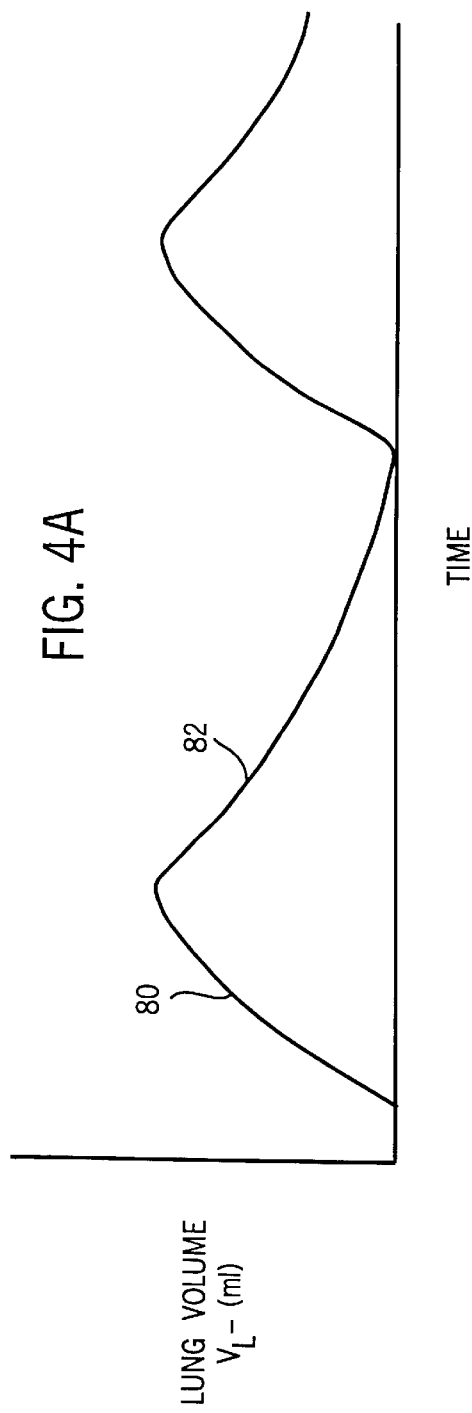
FIGS. 4A and 4B show the relationship between the volume of breathing gases in the lungs of a subject and pressures sensed in a pressure transducer inserted in a hollow organ of the subject.

FIG. 4A is a graph showing the inspiration of breathing gases into the lungs of subject 42 by ventilator 40 during inspiration and the discharge of gases from the lungs of the subject during expiration. As noted above, a typical breathing rate for subject 42 is 10–12 breaths per minute or about one breath every 3–5 seconds. The period of inspiration occupies approximately one third of the breathing cycle and the period of expiration, the remaining two thirds. During inspiration, a volume of breathing gases fills the lungs. The volume of the lungs rises from a resting level to a normal maximum level, as shown by the graph 80. Thereafter, the lungs contract as breathing gases are exhaled, as shown by the graph 82, either naturally or under the control of ventilator 40. The tidal volume of breathing gases inhaled and exhaled during each respiratory cycle is typically 400–700 ml per breath. The timing of the respiratory cycle and the tidal volume amount are determined by ventilator 40.

As ventilator 40 supplies breathing gases to the lungs of subject 42, the lungs of subject 42 will expand and increase in volume. The supply of breathing gases to the subject increases the pressure in the lungs which can be sensed by a pressure transducer in the pathway for the breathing gases of the subject. The volumetric expansion of the lungs also compresses other organs in the body, causing the internal pressure in hollow organs in the body to rise. Thus, as the lungs of subject 42 are inflated by breathing gases from ventilator 40, the pressure in the stomach containing catheter 20 will also rise.

Figure 4B:
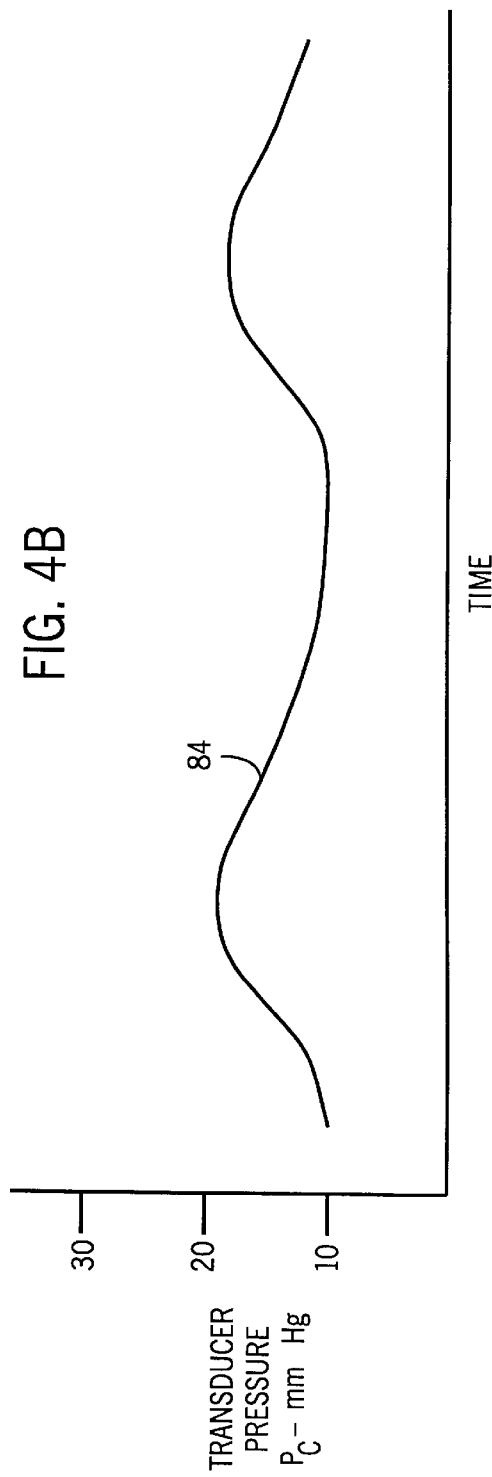

FIG. 4B illustrates the relationship between changes in lung volume and hollow organ pressures, using the pressure sensed by stomach catheter 20 as an example. As subject 42 inspires approximately 500 ml of breathing gases as indicated by graph 80 in FIG. 4A, the resulting compression of the stomach will increase the pressure in catheter balloon 22 by 10 millimeters of mercury (mmHg), (approximately 0.2 pounds per square inch) as shown by the graph 84 in FIG. 4B. When the breathing gases are expired by subject 42, and the volume of the lungs decreases, the pressure in catheter balloon 22 will similarly decrease, also as shown in FIG. 4B.

FIG. 6 shows the relationship between incremental changes in the volume of breathing gases, in the lungs of subject 42, as determined from flow sensor 68 in ventilator 40 and shown in FIG. 6A, and the resulting incremental change in the pressure as sensed by the pressure transducer and shown in FIG. 6B. The former is identified as $\Delta V_L$ and the latter is identified as $\Delta P_T$. The relationship between a change in volume and a change in pressure is often termed "compliance." However, it should be noted that compliance usually describes the relationship between changes in volume and pressure occurring in the same organ. This would be the case with a probe located along the breathing gasses pathway for the subject so that the relationship between a change in lung volume and a change in lung pressure is established. In the present instance "compliance", may also be used to describe changes in volume occurring in one organ, the lungs, and changes in pressure occurring in another organ, the stomach.

In a similar manner, but to a lesser extent, changes in the size, or volume, of the heart will also be reflected in the organ pressure sensed by the pressure transducer in fluid communication with the hollow organ of the subject. Thus, when the heart contracts during systole to discharge blood, its volume is reduced. The reduction in the size of the heart reduces the pressure on other organs of the body in the same manner as the expiration of breathing gases from the lungs and causes a reduction in the pressure sensed by the hollow organ pressure transducer, such as that associated with balloon 22. This phenomenon is shown in FIGS. 5A and 5B which are similar to FIGS. 4A and 4B except that the periodic reduction in pressure resulting from the contraction of the heart is shown in FIG. 5B in somewhat exaggerated form as 86. In the case of a catheter of the type shown in FIG. 2, the reduction in pressure sensed by the pressure transducer due to the contraction of the heart may, for example, be 0.5 or 1 mmHg. If catheter 20 is placed in the esophagus, pressure changes would tend to be amplified due the proximity of the esophagus to the lungs and heart. The volume of blood discharged from the heart is related to the size reduction of the heart inasmuch as the latter is due primarily to the blood discharging, ventricular contraction.

In accordance with the present invention, the phenomenon shown in FIGS. 4 and 5 can be used to determine the stroke volume or cardiac output of the heart in the following manner, and as more fully seen in FIGS. 6A and 6B. FIGS. 6A and 6B comprise the enlarged portion of FIGS. 5A and 5B identified in the latter. To carry out the stroke volume determination, the relationship between volumetric changes in the thoracic cavity and pressure changes sensed by the pressure transducer is first ascertained. The volume of breathing gas supplied to/removed from the lungs of subject 42 is obtained from flow sensor 68 during a first sampling period $T_0$–$T_1$. This provides the incremental quantity of breathing gas $\Delta V_L$ shown in FIG. 6A. Sampling interval $T_0$–$T_1$ is preferably Just before a heart beat by the subject, as shown in FIG. 6. The sampling interval can be established based on the heart rate of the patient and with an appropriate delay following a previous heart beat. Or, if an electrocardiographic signal is available, the sampling interval can be triggered based on the T or P waves of the electrocardiographic signal. As noted above, in connection with FIG. 1, the quiescent, diastolic interval between heart beats is about 400 ms, during which time incremental gas volume $\Delta V_L$ can be obtained.

In the same sampling interval, the pressure change sensed by the pressure transducer $\Delta P_T$ is also measured. In the instance of the present illustrative example, this would be the pressure in balloon 22, as shown in FIG. 6B. The relationship between a change in the volume of an organ in the thoracic cavity and a change in pressure in the hollow organ can be established as the ratio $\Delta V_L/\Delta P_T$. This ratio relates thoracic volume changes in milliliters (ml) to pressure transducer pressure changes in millimeters of mercury (mmHg).

A second sampling interval, for example $T_1$–$T_2$, preferably immediately. following the first sampling interval, includes the period during which the heart contracts to discharge blood. The contraction of the heart comprises a reduction in volume in the thoracic cavity which results in a pressure reduction in the hollow organ. The reduction in pressure 86 due to the ventricular contraction of the heart, termed $P_{TH}$ shown in FIG. 6B, is obtained, for example, from transducer 30 in catheter 20 in the second sampling interval. This pressure change can also be expressed in millimeters of mercury (mmHg) similarly to the pressure change $\Delta P_T$.

Knowing the pressure change $P_{TH}$ sensed in the hollow organ as a result of a heart contraction, and the relationship $\Delta V_L/\Delta P_T$ between hollow organ pressure change and volumetric changes in the thoracic cavity, the volumetric reduction in the size of the heart during systole, in milliliters, can be determined as $$V_{HR} = P_{TH} \times (\Delta V_L/\Delta P_T)$$

The stroke volume (SV) of the heart will be related to the volumetric reduction in the size of the heart and can be obtained from the quantity $V_{HR}$. Certain modifications may have to be made to the quantity $V_{HR}$ to arrive at stroke volume (SV). For example, because a pulmonary artery catheter has been used in the past to determine stroke volume, the term SV has come to mean the volume of blood discharged by one ventricle, i.e. the left ventricle serving the pulmonary artery. The quantity $V_{HR}$ determined above is the overall reduction of the volume of the heart due to the action of both ventricles so that the quantity $V_{HR}$ would have to be divided by a factor, most simplistically 2, to provide a stroke volume comparable to the conventional quantity.

Since the stroke volume of the heart thus determined is based on a determination of the actual, physical reduction in the size of the heart during systole, the value of the stroke volume from the quantity $V_{HR}$ is an absolute value, not a relative value. A correction of the incremental gas volume $\Delta V_L$, used to compute the stroke volume (SV), which is a liquid volume, may be necessary because the gas volume in the subject's lungs will be compressed. The gas volume $\Delta V_L$ is corrected in accordance with gas pressures in the subject's lungs. When the probe containing the pressure transducer is placed in the breathing gases passageway, the output of this transducer may be used to obtain the necessary correction. Or, a separate pressure sensor 69 may be provided in conduit 62 and connected to computational circuit 33 for this purpose, as shown in FIG. 3.

The cardiac output (CO) of the heart can be ascertained by determining and summing the stroke volumes of the heart beats occurring in a given time period, such as one minute.

As the output of the pressure transducer is supplied to computational circuit 33, circuit 33 may include timing circuitry that measures the duration or other temporal properties of pressure reduction 86 shown in FIGS. 5 and 6 to determine blood ejection times occurring with the functioning of the heart.

The method of the present invention utilizes the reduction in pressure $P_{TH}$ sensed by the pressure transducer to measure the corresponding reduction in heart size, and hence stroke volume. To improve the accuracy of the measurement, it is deemed preferable to use values of $\Delta V_L$ and $\Delta P_T$ obtained when the volume of the lungs is also decreasing, i.e. during expiration by subject 42. This is as shown in FIG. 6. Also, as will be appreciated from the graphs of FIGS. 4, 5, and 6, the relationship of $\Delta V_L$ to $\Delta P_T$ changes throughout the respiratory cycle. Thus, determining a compliance value or ratio ($\Delta V_L/\Delta P_T$) immediately before sensing a succeeding pressure reduction $P_{TH}$ resulting from a heart beat enables an appropriate value of the former to be applied to the latter and also improves the accuracy of stroke volume determination.

While FIG. 6 shows the principle of the present invention in connection with a single heart beat, it will be appreciated that determinations made in the foregoing manner can be carried out on a beat-by-beat basis for each heart beat of the subject or for a selected plurality of heart beats, such as those occurring during expiration. The values obtained from multiple measurements may be subjected to averaging or other statistical analysis to arrive at a value for stroke volume. For example, the stroke volume may be calculated as the average stroke volume determined from the individual stroke volumes obtained over a full respiration cycle. Also, while the method of the present invention has been described as using discrete sampling intervals, it will be appreciated that lung volume and organ pressures may be continuously monitored, if desired.

The absolute values for stroke volume and cardiac output obtained by the above described method can be used for calibration in one or more of the known methods producing relative values, thereby avoiding the need to perform pulmonary artery catheterization of the subject to obtain absolute values of desired cardiac characteristics by the known methods.

As noted above, the ventricular, systolic contraction that produces the pressure reduction 86 sensed by the pressure transducer in the hollow organ occupies about 400 ms. It is thus desirable that the pressure transducer have frequency response characteristics capable of sensing transient phenomena of such nature. It is presently deemed preferable that the frequency response characteristics of the pressure transducer be at least 2 Hz, more preferably 5 to 10 Hz.

A number of factors relate to the frequency response of the pressure transducer and the magnitude of the signal obtained therefrom. These factors include the selection of the hollow organ which is used to obtain the pressure change amounts $\Delta P_T$ and $P_{TH}$. Where for example, the pressure transducer is in fluid communication with the lungs of the subject, the factors may include location of the transducer along the breathing gases passageway extending from ventilator 40 to the lungs of the subject. While, it has been described above to locate the pressure transducer in proximity to an endotraclieal tube for the subject, it will be appreciated that the pressure transducer can be located further into the subject's respiratory tract toward or into the lungs. Or, the pressure transducer may be located further away from the subject's lungs as in the conduits 62, 58, 50, etc. of ventilator 40. The magnitude of the sampling interval $T_1$=$T_2$ should be selected such that the transient pressure change is fully captured. When a catheter of the type shown in FIG. 2 is employed, the fluid used in the catheter affects frequency response, with a liquid filled catheter having a higher frequency response than a gas filled catheter.

Obtaining the relationship between a volumetric change in the lungs and the corresponding pressure change in the hollow organ has been described above as obtained in a dynamic fashion. That is, at any given sampling interval in the respiratory cycle, the volumetric change in the lungs is determined and the corresponding change in hollow organ pressure ascertained. Also as noted above, the ratio of the two quantities. will change during the respiratory cycle, and particularly between the inspiration and expiration phases of the respiratory cycle. This is particularly true when the lungs are used as the hollow organ in which pressure changes $\Delta P_T$ and $P_{TH}$ are obtained, since, on a dynamic basis, the same lung pressure reading may occur at a different lung volume during inspiration than during expiration. For this and other reasons, it may be desirable to develop a static compliance curve for the subject's lungs for use in determining stroke volume. A static compliance curve is produced by supplying a small increment of breathing gas volume to the subject's lungs, allowing the condition of the subject's lungs to stabilize, measuring lung pressure after stabilization, and repeating this process to obtain the curve. The relationship between incremental lung volume change $\Delta V_L$ and incremental pressure change $\Delta P_T$ used to determine stroke volume would be taken from the static compliance curve.

Figure 7A:
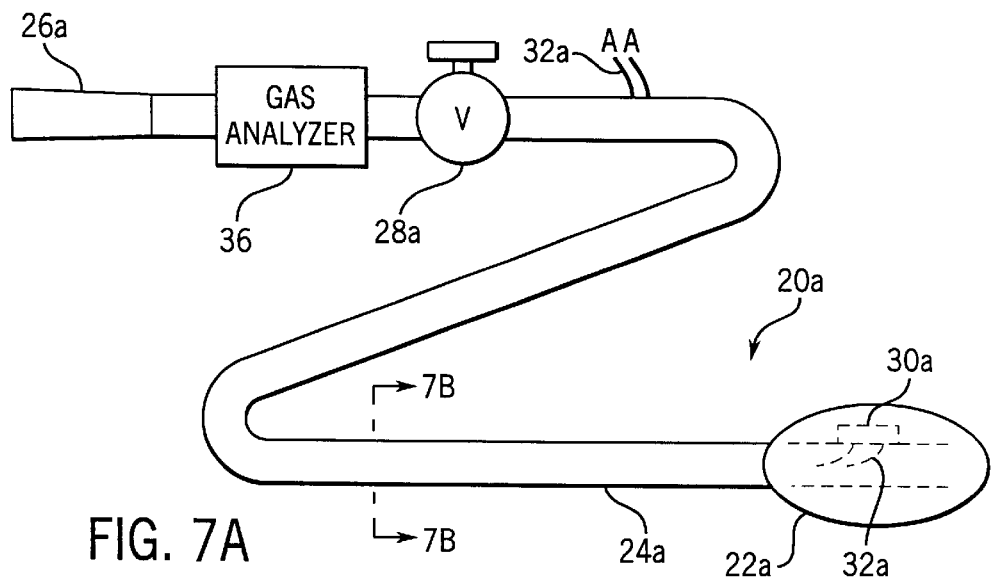
FIGS. 7A and 7B show a modified catheter apparatus with which tonometric measurements may also be taken.
Figure 7B:
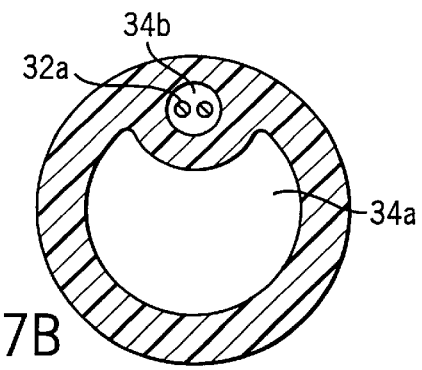
Figure 8A:
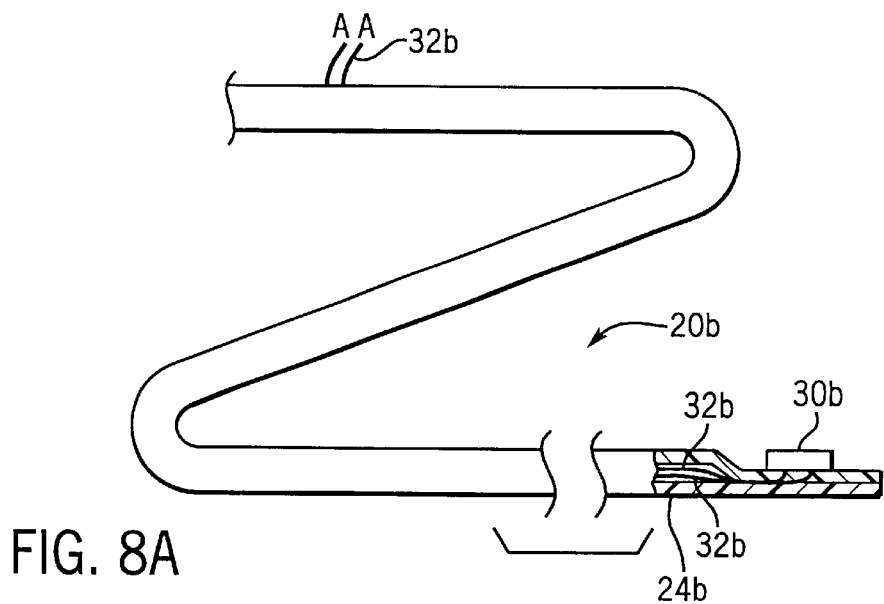
FIGS. 8A and 8B show further pressure transducer devices for carrying out the method of the present invention.
Figure 8B:
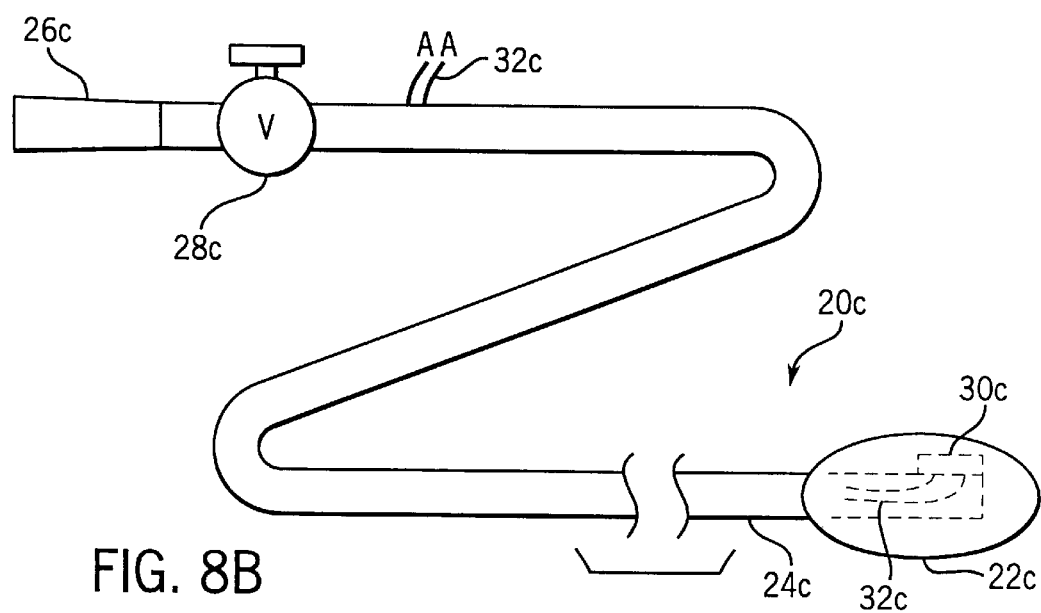

While FIGS. 2 and 7 show catheters in which the pressure transducer is in a balloon, pressure transducer 30 may also be placed directly in the hollow organ of the subject through use of a probe or catheter of the type shown in FIG. 8A. Such a probe 20b has pressure transducer 30b mounted on the end of the probe placed in the hollow organ of the subject. Electrical wires 32b leading from pressure transducer 30b pass through a lumen of tube 24b and exit the tube at the second end of the tube outside the body of the subject. Such a probe may be used when the hollow organ used in the method is the lungs Or, as shown in FIG. 8B, pressure sensor 30c may be placed in a fluid filled balloon 22c connected to one end of tube 24c. The connecting wires 32c for pressure sensor 30c run through a lumen of tube 24c to exit at the second end of tube 24c remaining outside the body. Luer lock 26c and valve 28c are provided to control the fluid supply to balloon 22c. The catheter 20c shown in FIG. 8B would tend to have higher frequency responses than that shown in FIG. 2 since pressure changes do not need to be transmitted up tube 24 to be sensed by the pressure transducer. This avoids the delays encountered with the catheter shown in FIG. 2 if air is used as the fluid medium. For that reason it may be preferable to use catheter of the type shown in FIG. 8 in practicing the present invention or to use a liquid medium in the catheter of FIG. 2.

When a catheter of the balloon type is used in the breathing gases pathway for the subject to measure pressures in the lungs, it will be appreciated that the balloon may be in the nature of a cuff surrounding a breathing tube for the subject. The pressure transducer may be placed in the cuff in the manner shown in FIG. 8B.

A further feature of the present invention is the ability to combine measurements of cardiac functioning with tonometric measurements in a hollow organ of the subject, such as the stomach or urinary bladder. In tonometric measurements, a catheter similar to that shown in FIGS. 2, 7, and 8B, is used to obtain the partial pressure of one or more gases, such as $CO_2$ or $O_2$, existing in the fluids or mucosa of the hollow organ in which the catheter is placed. For this purpose, the balloon 22 of the catheter 20 is made of a material, such as silicone, that is permeable to the gas, the partial pressure of which is to be measured. After balloon 22, filled with air or water, has remained in the hollow organ for a sufficient period of time, the partial pressure of, for example $CO_2$, in the fluid in the balloon reaches equilibrium with the partial pressure $pCO_2$ in the organ. The fluid in balloon 22 is then removed and passed through a gas analyzer to determine the level of $CO_2$ or $O_2$ in the hollow organ. These quantities may be used to determine the physiological state of the organ and/or the subject. Balloon 22 may then be reinflated with fluid and the tonometric and cardiac measurements repeated. Or, fluid containing the gas permeated through balloon 22 may be continuously recirculated between the balloon and a gas analyzer to provide continuous measurement.

In the catheter shown in FIGS. 7A and 7B tube 24a of catheter 20a has two lumens. One lumen 34a comprises a fluid passage to and from gas permeable balloon 22a for supplying fluid to balloon 22a. The other lumen 34b comprises a passage for connecting wires 32a for pressure transducer 30b which, in catheter 20a, has been placed in balloon 22a. A syringe, not shown, may be fastened to luer lock 26a to withdraw a fluid, such as air, from balloon 22a through gas detector 36, which may, for example, comprise an infrared $CO_2$ detector. Catheters similar to catheters 20, 20a, 20c suitable for use in tonometry and associated measuring apparatus for the catheter are described in one or more of the following U.S. Pat. Nos. 4,643,192; 5,174,290; and 5,186,172.

While FIG. 3 shows use of a mechanical ventilator 40 to provide breathing gas to the subject, as noted above, the method of the present invention may be used with a spontaneously breathing subject in which atmospheric air pressure, rather than ventilation breathing gas pressure is used to increase the volume of the lungs. Such a subject could breathe through a tube, corresponding to conduit 62, containing flow sensor 68 and a pressure sensor 69.

Figure 9:
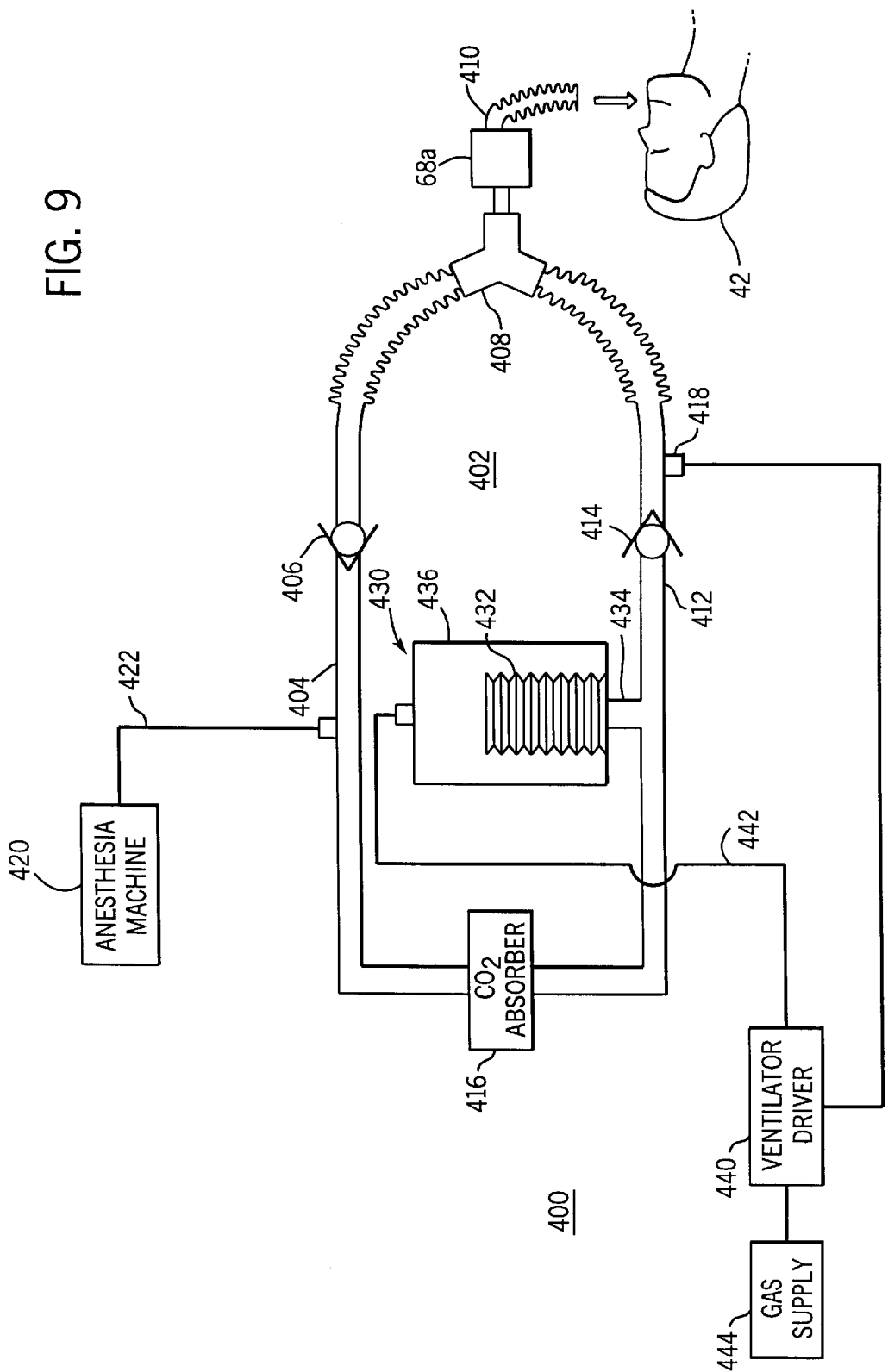
FIG. 9 shows an alternative embodiment of ventilator apparatus suitable for use in the method of the present invention.

FIG. 9 shows a ventilator 400 of the closed circuit type for mechanically ventilating subject 42. In ventilator 400 the driving gas used to move the breathing gases to and from the subject's lungs is separated from the breathing gases actually delivered to the subject's lungs. The breathing gases are re-breathed by the subject. The closed circuit enables anesthesia, or other drugs, to be added to the subject's breathing gases and prevents the loss of such drugs to the environment.

Ventilator 400 includes breathing circuit 402 which includes inspiration limb 404 having inspiration check valve 406. Inspiration limb 404 is connected to an inlet of Y-connector 408. Patient limb 410 of Y-connector 408 supplies breathing gases to subject 42 during inspiration and receives respiratory gases from the subject during expiration. Flow sensor 68a may be positioned in patient limb 410. Breathing circuit 402 also includes an exhalation limb 412. Expiration limb 412 is connected to an output of Y-connector 408 and includes expiration check valve 414. If only the inspiration phase or the expiration phase of the subject's breathing cycle is used to measure cardiac stroke volume, flow sensor 68a may be placed in the appropriate limb, if desired. Expiration limb 412 is connected to the inlet of carbon dioxide ($CO_2$) absorber 416, the outlet of which is connected to inspiration limb 404 to complete the closed circuit breathing system. $CO_2$ absorber 416 may contain soda lime or other suitable $CO_2$ absorbent. A pressure sensor 418 may be connected in breathing circuit 402, as in expiration limb 412 to detect the pressure in breathing circuit 402. If breathing circuit 402 is being used in conjunction with an anaesthesia machine, such as that indicated by the numeral 420, the anaesthesia machine may be connected to inspiration limb 404 by conduit 422 to provide anaesthetic agents, as needed.

Bellows assembly 430 is used to separate the breathing gases in breathing circuit 402 from the driving gas. Bellows assembly 430 includes expandable, pleated bellows 432. Bellows 432 is connected to expiration limb 412 by pipe 434. Bellows 432 is contained in housing 436. In a typical ventilator, bellows 432 expands upwardly and contracts downwardly in housing 40.

Bellows assembly 430 is operated by ventilator driver 440 which is coupled to housing 436 by a supply line 442. Gas supply 444 shown in FIG. 3 may comprise a source of air, nitrogen, or other driving gas.

To supply breathing gases to subject 42, ventilator driver 440 is operated to supply driving gas to housing 436 of bellows apparatus 430 via supply line 442. The gas so supplied compresses bellows 432 downwardly, forcing the breathing gases in the bellows and in the downstream portions of breathing circuit 402 through $CO_2$ absorber 416, inspiration limb 404, and Y-piece connector 408 to subject 42. The volume of breathing gases delivered to subject 42 is determined by the amount of driving gas. During expiration, the driving gas in housing 436 is allowed to exit the housing, permitting bellows 432 to expand upwardly and receive the exhaled gases as subject 42 breathes out The exhaled gases are provided to bellows 432 via expiration limb 412 and exhalation check valve 414. The volume of breathing gas delivered to/received from subject 42 is measured by flow sensor 68a.

On the next breath for subject 42, bellows 432 is again compressed by the driving gas to provide breathing gases to the subject. The $CO_2$ in the breathing gas previously exhaled by the subject and contained in bellows 432 is removed by $CO_2$ absorber 416 and the breathing gases pass through inspiration limb 404 for delivery to subject 42. The breathing gases subsequently exhaled by the subject are again received in expiration limb 412 and bellows 432.

Other embodiments of the invention are contemplated as being within the scope of the appended claims.

What is claimed is:

1. A method for determining a desired physiological characteristic relating to the blood circulating action of the he art of a subject, said method comprising the steps of:
   (a) carrying out an incremental change in the volume ($\Delta V_L$) of breathing gas in the subject's lungs;
   (b) measuring the corresponding change in pressure ($\Delta P_T$) in an organ of the subject, other than a blood vessel, resulting from an incremental change in breathing gas volume in the subject's lungs;
   (c) determining the relationship between an incremental change in breathing gas volume ($\Delta V_L$) and a resulting incremental change in pressure ($\Delta P_T$) in the organ;
   (d) measuring the change in pressure ($\Delta P_{TH}$) in the organ caused by volumetric changes of the subject's heart occurring from blood circulating action; and
   (e) determining from the change in pressure ($\Delta P_{TH}$) and the $\Delta V_L$-$\Delta P_T$ relationship, the amount of the volumetric change in the subject's heart and the desired physiological characteristic.

2. A method according to claim 1 wherein step (e) is further defined as determining the stroke volume (SV) of the subject's heart.

3. A method according to claim 2 further defined as summing the stroke volumes of heart beats occurring in a predetermined period of time to determine cardiac output (CO) of the subject's heart.

4. A method according to claim 2 wherein the determination of stroke volume is an absolute value for stroke volume (SV), said method using the value of stroke volume determined in step (e) to calibrate a relative value of stroke volume (SV) determined by a different method.

5. A method according to claim 1 wherein step (e) is further defined as determining the stroke volume (SV) for each of a plurality of heart beats of the subject and the method includes the step of subjecting the determination made in step (e) to a mathematical process to determine the desired characteristic.

6. A method according to claim 1 further defined as including the step of placing a pressure transducer in fluid communication with a hollow organ of the subject to carry out the measurements of steps (b) and (d).

7. A method according to claim 6 further defined as placing the pressure transducer in fluid communication with the hollow organ in a manner to provide frequency response characteristics sufficient to carry out the measurement of step (d).

8. A method according to claim 7 further defined as providing a frequency response of at least 2 Hz in the pressure transducer for carrying out the measurement of step (d).

9. A method according to claim 6 wherein the step of placing the pressure transducer in fluid communication with the hollow organ is further defined as placing the pressure transducer in the hollow organ.

10. A method according to claim 9 further defined as placing the pressure transducer in the hollow organ without the use of invasive surgical intervention.

11. A method according to claim 6 wherein the step of placing the pressure transducer in fluid communication with the hollow organ is further defined as placing a fluid filled member in the hollow organ for transmitting the pressure in the hollow organ to the pressure transducer.

12. A method according to claim 11 is further defined as placing one end of an elongated fluid filled member in the hollow organ with the other end extending out of the body of the subject and wherein the pressure transducer is coupled to the other end of the member for measuring pressure in the hollow organ transmitted through the fluid.

13. A method according to claim 11 further defined as placing a liquid filled member in the hollow organ.

14. A method according to claim 11 further defined as placing a gas filled member in the hollow organ.

15. A method according to claim 11 further defined as including the step of carrying out tonometric measurements in the hollow organ using the fluid filled member.

16. A method according to claim 1 further defined as carrying out the measurements of steps (b) and (d) in the lungs of the subject.

17. A method according to claim 16 wherein a breathing gas pathway extends to the subject's lungs and wherein the measurements of steps (b) and (d) are carried out at a selected location along the breathing gas pathway.

18. A method according to claim 1 further defined as carrying out the measurements of steps (b) and (d) in a hollow organ of the subject other than the lungs.

19. A method according to claim 18 further defined as carrying out the measurements of steps (b) and (d) in the digestive tract of the subject.

20. A method according to claim 19 further defined as carrying out the measurements of steps (b) and (d) in the stomach of the subject.

21. A method according to claim 18 further defined carrying out the measurements of steps (b) and (d) in the urinary bladder of the subject.

22. A method according to claim 18 further defined as carrying out the measurements of steps (b) and (d) in the esophagus of the subject.

23. A method according to claim 1 further defined as carrying out the steps of the method on a spontaneously breathing subject.

24. A method according to claim 1 wherein step (a) is further defined as providing and removing breathing gases to/from the lungs of the subject.

25. A method according to claim 24 wherein step (a) is further defined as providing breathing gases by mechanical ventilation.

26. A method according to claim 1 wherein the subject breathes in respiratory cycles having an inspiratory phase and an expiratory phase and wherein steps (a), (b), and (d) are carried out during the expiratory phase of a respiratory cycle.

27. A method according to claim 25 wherein steps (a) and (b) are carried out in a first sampling period and step (d) is carried out in a second sampling period.

28. A method according to claim 27 wherein said second sampling period follows said first sampling period.

29. A method according to claim 1 further defined as carrying out steps (a) and (b) in a first sampling period and as carrying out step (d) in a second sampling period.

30. A method according to claim 29 wherein said second sampling period follows said first sampling period.

31. A method according to claim I wherein the volumetric change of the subject's heart has temporal properties and wherein the method includes the step of measuring the temporal properties of the volumetric change to determine ejection time characteristics of the heart.

* * * * *